(12) United States Patent
Scott

(10) Patent No.: US 8,730,316 B2
(45) Date of Patent: May 20, 2014

(54) CABLE APPARATUS

(75) Inventor: Joshua Lynn Scott, Jordan, NY (US)

(73) Assignee: General Electric Company, Schenectady, NY (US)

( * ) Notice: Subject to any disclaimer, the term of this patent is extended or adjusted under 35 U.S.C. 154(b) by 367 days.

(21) Appl. No.: 13/033,732

(22) Filed: Feb. 24, 2011

(65) Prior Publication Data

US 2012/0218401 A1 Aug. 30, 2012

(51) Int. Cl.
*H04N 7/18* (2006.01)
*H04N 5/225* (2006.01)

(52) U.S. Cl.
CPC .................................. *H04N 5/2259* (2013.01)
USPC ......................................................... 348/82

(58) Field of Classification Search
CPC ................... H04N 5/2259; H04N 2201/3252; H04N 2007/145
USPC ....................... 348/82; 600/109, 129; 359/811
IPC ....................................................... H04N 7/18
See application file for complete search history.

(56) References Cited

U.S. PATENT DOCUMENTS

| | | | |
|---|---|---|---|
| 5,547,301 A | 8/1996 | Kageyama et al. | |
| 5,671,833 A | 9/1997 | Edwards et al. | |
| 5,754,220 A | 5/1998 | Smalser, Sr. | |
| 6,340,261 B1 | 1/2002 | Furukawa | |
| 6,545,704 B1 | 4/2003 | Olsson et al. | |
| 6,773,185 B1 | 8/2004 | Hsieh | |
| 7,452,149 B2 | 11/2008 | Saito | |
| RE41,467 E | 8/2010 | Saito et al. | |
| 7,780,650 B2 | 8/2010 | Frassica et al. | |
| 2002/0123664 A1* | 9/2002 | Mitsumori | 600/130 |
| 2007/0135803 A1 | 6/2007 | Belson | |
| 2009/0005645 A1 | 1/2009 | Frassica et al. | |
| 2009/0303619 A1* | 12/2009 | Iwasaki et al. | 359/811 |
| 2010/0129131 A1 | 5/2010 | Liu | |
| 2010/0240955 A1 | 9/2010 | Sinai et al. | |
| 2011/0009694 A1* | 1/2011 | Schultz et al. | 600/109 |

FOREIGN PATENT DOCUMENTS

EP 2130482 A1 12/2009
WO 2010004752 A1 1/2010

OTHER PUBLICATIONS

Search Report and Written Opinion from EP Application No. 12156436.3 dated Jun. 29, 2012.

* cited by examiner

*Primary Examiner* — Jay Au Patel
*Assistant Examiner* — Neil Mikeska
(74) *Attorney, Agent, or Firm* — Hiscock & Barclay LLP

(57) ABSTRACT

A cable apparatus is provided and includes a cable to assume discrete positions, an actuator operably coupled to the cable and including a power source and a cable unit, which, when activated, causes the cable to translate and draws power from the power source and, when deactivated, draws no power and permits cable translation and a housing operably disposed along the cable and including a first element that rotates and translates with respect to the cable and a second element fixed to the cable, the first element being configured to cause the second element to rotate.

20 Claims, 4 Drawing Sheets

CABLE APPARATUS

BACKGROUND OF THE INVENTION

The subject matter disclosed herein relates to a cable apparatus.

In various industries, generating images of components can assist operators in determining whether those components are operating within normal parameters or require repair or replacement. In the case of gas turbine engines, for example, certain components in the interior of the engines experience high operational temperatures and pressures and tend to deteriorate over time. In these cases, however, the components can be difficult to access and it becomes necessary to snake cables into the engine interiors in order to position imaging devices disposed at the ends of those cables near the components being studied.

Once the imaging devices are appropriately positioned, they can be employed to generate the desired images for display on a handheld device attached to the other end of the cable. This handheld device is generally portable and battery powered.

In some instances, it becomes apparent that the image being generated is either inadequate or needs to be supplemented by a further image of the object at a different zoom state. Currently, this different zoom state is achieved by the handheld device being instructed by the operator to act upon the cable to change its length and to thereby bring the imaging device closer to or farther from the components being studied. The action of the handheld device on the cable is power intensive, however, and must be maintained for as long as the different zoom state is needed. This represents a substantial drain on limited resources.

BRIEF DESCRIPTION OF THE INVENTION

According to one aspect of the invention, a cable apparatus is provided and includes a cable to assume discrete positions, an actuator operably coupled to the cable and including a power source and a cable unit, which, when activated, causes the cable to translate and draws power from the power source and, when deactivated, draws no power and permits cable translation and a housing operably disposed along the cable and including a first element that rotates and translates with respect to the cable and a second element fixed to the cable, the first element being configured to cause the second element to rotate.

According to another aspect of the invention, a cable apparatus is provided and includes a cable to assume discrete positions, a device disposed on the cable to generate an image in first or second zoom states respectively associated with each of the positions, an actuator operably coupled to the cable and the device and including a power source, a display unit to display the image, and a cable unit, which, when activated, causes the cable to translate and draws power from the power source and, when deactivated, draws no power and permits cable translation and a housing operably disposed along the cable and including a first element that rotates and translates with respect to the cable and a second element fixed to the cable, the first element being configured to cause the second element to rotate.

According to yet another aspect of the invention, a cable apparatus is provided and includes a cable to assume one of first, second and third discrete positions, an actuator operably coupled to the cable and including a power source and a cable unit, which, when activated, causes the cable to initially translate from the first position to the second position and draws power from the power source and, when deactivated, draws no power and permits the cable to secondarily translate from the second position to the third position and a housing disposed along the cable and including a first assembly to urge the cable to secondarily translate from the second position to the third position, and a second assembly including a first element that rotates and translates with respect to the cable and a second element fixed to the cable, the first element being configured to cause the second element to rotate to thereby urge the cable toward assumption of the third position.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
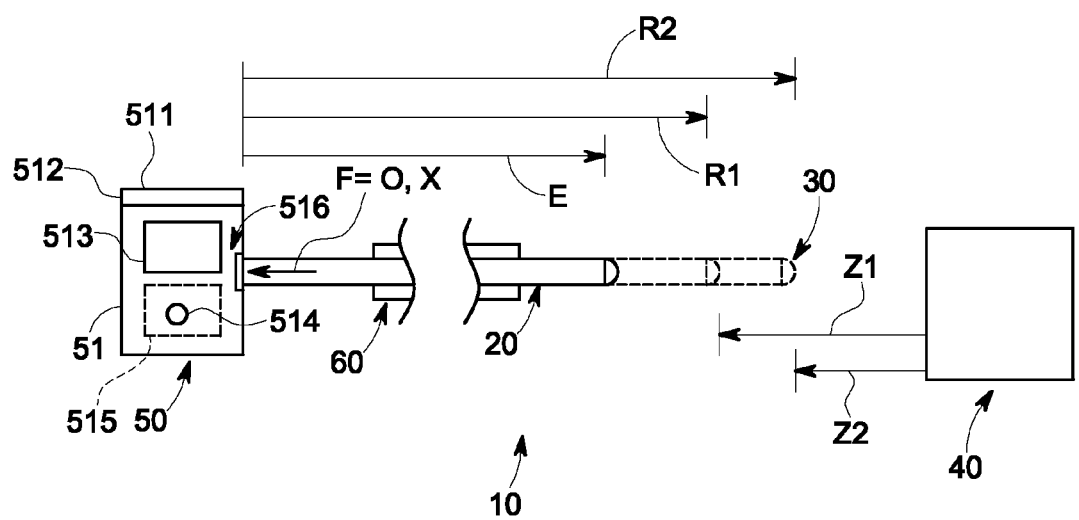
FIG. 1 is a side schematic view of a cable apparatus.

With reference to FIG. 1, a cable apparatus 10 is provided. The cable apparatus 10 is relatively thin for insertion and/or snaking into a machine. The cable apparatus 10 includes a cable 20 to assume one of an energized position, E, and multiple discrete rest positions, such as first rest position, R1, and second rest position, R2. A device 30 such as a camera or some other similar image forming device is disposed on the cable 20 to generate an image of, for example, an object 40 in first or second zoom states, Z1 and Z2, which are respectively associated with the first and second rest positions, R1 and R2. The cable apparatus 10 further includes an actuator 50 that is operably coupled to the cable 20 and the device 30 and a housing 60.

The energized position, E, and the multiple discrete rest positions are each characterized by a unique cable 20 length. Each unique cable 20 length may be measured from a common reference point, such as, for example, an edge of the actuator 50.

The actuator 50 may include a handheld device 51, where the handheld device 51 has a body 511 that is appropriately sized to be held by an operator for imaging operations and portability, a power source 512 for operably housing a battery that may be removable and/or rechargeable, a display unit 513 to display the image generated by the device 30, an input unit 514, a processor 515 and a cable unit 516. The cable unit 516 is temporarily activatable to cause the cable 20 to translate from a previously assumed one of the multiple rest positions and draws power from the power source 512 only when temporarily activated. The input unit 514 may be a single button, for example, by which a single command for temporarily activating the cable unit 516 is input by the operator and thereby receivable by the processor 515. The processor 515 is programmed with executable instructions, which, when executed, cause the processor 515 to conduct at least one or more activation/deactivation cycles of the cable unit 516 upon receipt of the single command.

The cable 20 is coupled to the actuator 50 at or proximate to the cable unit 516. When temporarily activated, the cable unit 516 may mechanically or electro-magnetically act upon the cable 20 with a force, F, by a pulling effect of servos, leadscrews, solenoids, etc. The cable unit 516 may also thermally act upon the cable 20. In this case, the cable 20 may be formed of memory metal (e.g., a TiNi alloy) and may be heated by, for example, electrical resistivity associated with an electrical current that is carried by the cable 20 as applied by the cable unit 516 to thereby shorten at least a section of the cable 20 by approximately 5%. This shortening leads to a result similar to that attained by the pulling effect. In each case, the action is temporary and leads effectively to an initial translation of the cable 20 from a previously assumed one of the multiple rest positions toward the energized position, E. From the energized position, E, the cable unit 516 is deactivated and the cable 20 accordingly assumes or is urged to assume a next one of the multiple rest positions, which is different from the previously assumed one of the multiple rest positions.

The cable unit 516 only draws power from the power source 512 during the temporary activation thereof and does not draw significant amounts of power during the deactivation thereof or when the cable 20 assumes any of the multiple rest positions. Thus, limited power resources of the power source 512 are drawn upon for only limited periods of time (i.e., when the cable unit 516 is temporarily activated) and power reserves of the power source 512 can therefore be conserved.

Figure 2:
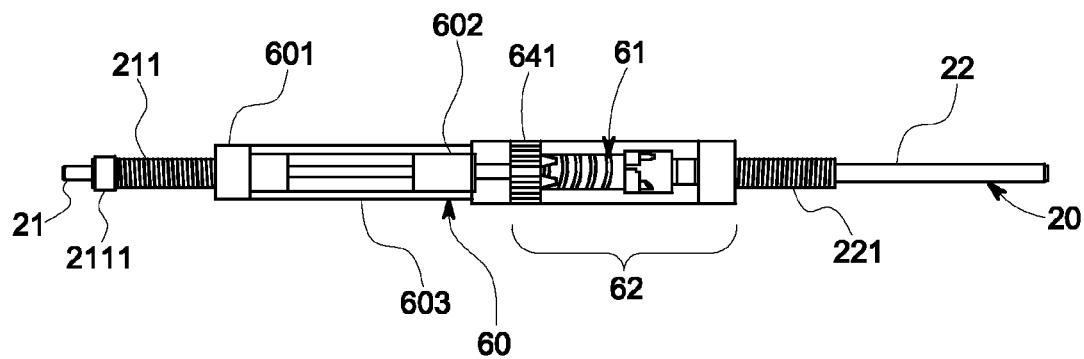
FIG. 2 is an enlarged view of a housing of the cable apparatus of FIG. 1.

With reference to FIGS. 1 and 2, the housing 60 is disposed along the cable 20 and includes a first assembly 61 and a second assembly 62. The first assembly 61 is configured to urge the cable 20 to secondarily translate from the energized position, E, to the next one of the multiple rest positions, which is different from the previously assumed one of the multiple rest positions. The second assembly 62 is configured to urge the cable 20 toward assumption of the next one of the multiple rest positions, during at least one or both of the initial and secondary translations of the cable 20.

The housing 60, the first assembly 61 and the second assembly 62 may have multiple embodiments all of which are within the scope of this disclosure. For purposes of clarity and brevity, however, only the embodiments of FIGS. 2-4 will be described herein.

Figure 3:
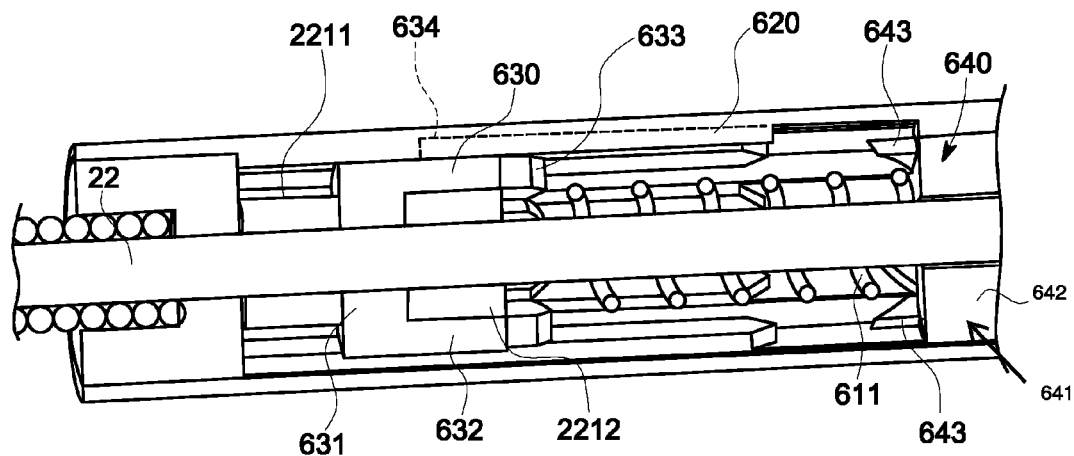
FIG. 3 is a perspective view of the housing of FIG. 2.
Figure 4:
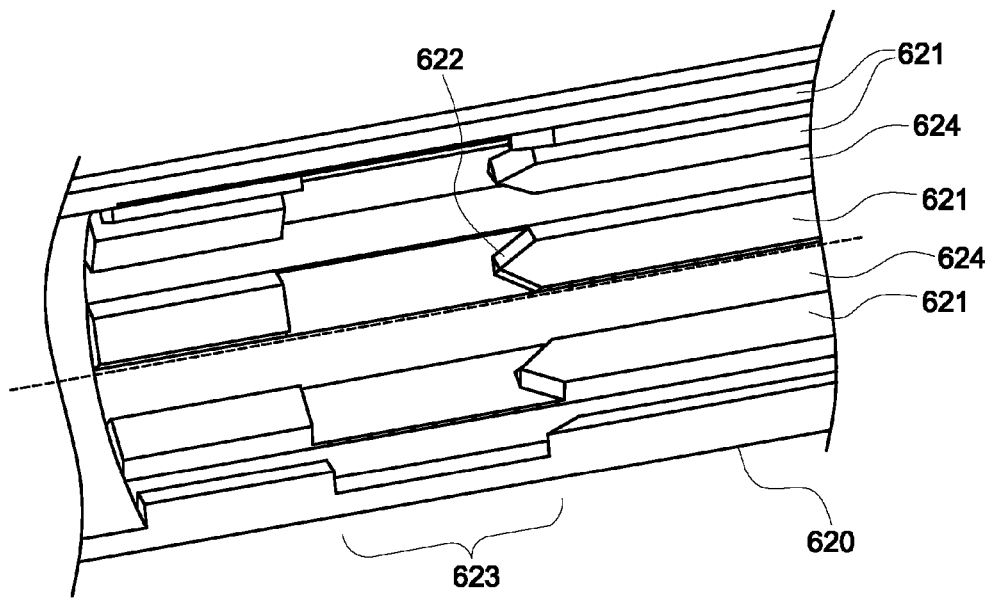
FIG. 4 is another perspective view of the housing of FIG. 2.

With reference to FIGS. 2-4 and, in accordance with those embodiments, the first assembly 61 may include an elastic element 611 to bias the cable 20 toward the multiple rest positions. The second assembly 62 may include an outer collar 620, a position collar 630 and an indexing system 640. The outer collar 620 and the indexing system 640 cooperatively form a first element that is rotatable and translational with respect to the cable 20. By contrast, the position collar 630 forms a second element that is rotationally and translationally fixed with respect to the cable 20.

The outer collar 620 is formed to define the multiple discrete rest positions, R1 and R2. The position collar 630 is fixedly coupled to the cable 20 and is receivable by the outer collar 620 in multiple orientations that are respectively associated with the multiple discrete rest positions, R1 and R2. The indexing system 640 urges the position collar 630 and the outer collar 620 to cooperatively assume a next one of the multiple orientations that is different from a previously assumed one of the multiple orientations during at least one or both of the initial and secondary translations of the cable 20.

As shown in FIGS. 2-4, the cable 20 may have a first section (hereinafter referred to as a "pull cable") 21 to which the actuator 50 is operably coupled and a second section (hereinafter referred to as an "application cable") 22 on which the device 30 is disposed. Opposing ends of the pull cable 21 and the application cable 22 are defined to terminate at the housing 60. The pull cable 21 is acted upon by the cable unit 516 of the actuator 50, as described above, when the cable unit 516 is temporarily activated and is translated accordingly.

A first cable sheath 211 supportively surrounds the pull cable 21 and a second cable sheath 221 supportively surrounds the application cable 22. The first cable sheath 211 is anchored on the first cable terminator 2111 that may itself be anchored on the actuator 50, for example. The first cable sheath 211 acts a spine that allows the pull cable 21 to generate a load against a sheath stop 601, which is disposed at an end of the housing 60 and which also aligns and holds the first cable sheath 211 in position.

As shown in FIG. 3, the pull cable 21 continues to extend through the sheath stop 61 and terminates toward the application cable 22 via a cable splice terminator 602, which is disposed at a mid-section of the housing 60 where displacement of the cable splice terminator 602 is guided within a cable splice guide 603 and occurs in accordance with translation of at least the pull cable 21. The application cable 22 extends from the cable splice terminator 602 through remaining components of the housing 60 and extends to the device 30. Along this length, the application cable 22 has a first cable terminator 2211 and a second cable terminator 2212 positioned on either side of the position collar 630. As the pull cable 21 is pulled, the cable splice terminator 602 and the application cable 22 are correspondingly pulled. As the application cable 22 is pulled, the pulling load is transferred to the first cable terminator 2211 which, in turn, causes the position collar 630 to displace and thereby compress an elastic element 611, such as a position collar spring.

The position collar 630 is an annular member having a base 631 abutting the first cable terminator 2211 and a ring section 632 perimetrically surrounding the application cable 22. The ring section 632 has an annular shape and defines an annular region between an inner surface thereof and an outer surface of the application cable 22 in which the elastic element 611 is nested. The position collar 630 further includes first parts 633 at an edge of the ring section 632 and second parts 634 at an outer surface of the ring section 632.

Figure 5A:
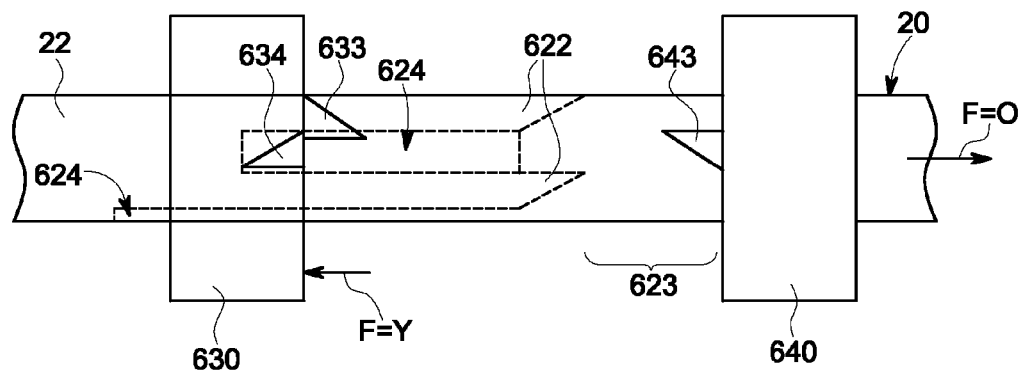
FIGS. 5A-5D cooperatively illustrate a sequential operation of the cable apparatus.

With reference now to FIGS. 3, 4 and 5A, the position collar 630 is initially axially displaced with a force, F, being applied to the cable 20 by the cable unit 516 increasing from zero magnitude to magnitude, X, which exceeds a force, Y, which is applied by the elastic element 611 to the position collar 630. As the position collar 630 is initially axially displaced, the position collar 630 is rotationally secured by the outer collar 620. As shown in FIGS. 3 and 4, the outer collar 620 is an annular member having circumferentially arrayed fingers 621 with third parts 622 adjacent to a relief cut section 623. The fingers 621 extend along and are arrayed about the application cable 22 and are separated from one another to thereby define depth setting channels 624.

Figure 5B:
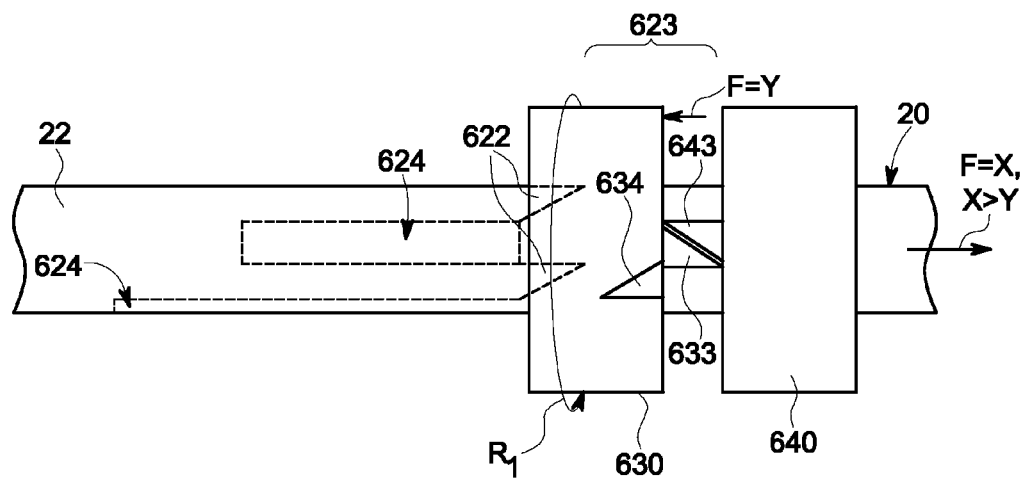

As shown in FIG. 5A, the second parts 634 of the position collar 630 are rotationally constrained within the depth setting channels 624 during the initial axial displacement of the position collar 630 until, as shown in FIG. 5B, the position collar 630 reaches the relief cut section 623 and the second parts 634 axially clear the third parts 622. That is, the position collar 630 continues to be rotationally secured during the axial displacement thereof, until the position collar 630 reaches the relief cut section 623 at which point the position collar 630 is free to rotate about an axis of the application cable 22, which extends through both the outer collar 620 and the position collar 630.

As the position collar 630 continues to be axially displaced, the indexing system 640 urges the position collar 630 and the outer collar 620 to cooperatively assume by at least rotation, $R_1$, about the application cable 22, a next one of the multiple orientations. The indexing system 640 includes indexer 641. As shown in FIGS. 3 and 4, the indexer 641 is an annular member having a ring section 642 disposed about the application cable 22 and abutment parts 643 extending from an edge of the ring section 642. The ring section 642 has an annular shape through which the application cable 22 extends and defines an annular region between an inner surface thereof and the outer surface of the application cable 22 in which the elastic element 611 is nested.

Figure 5C:
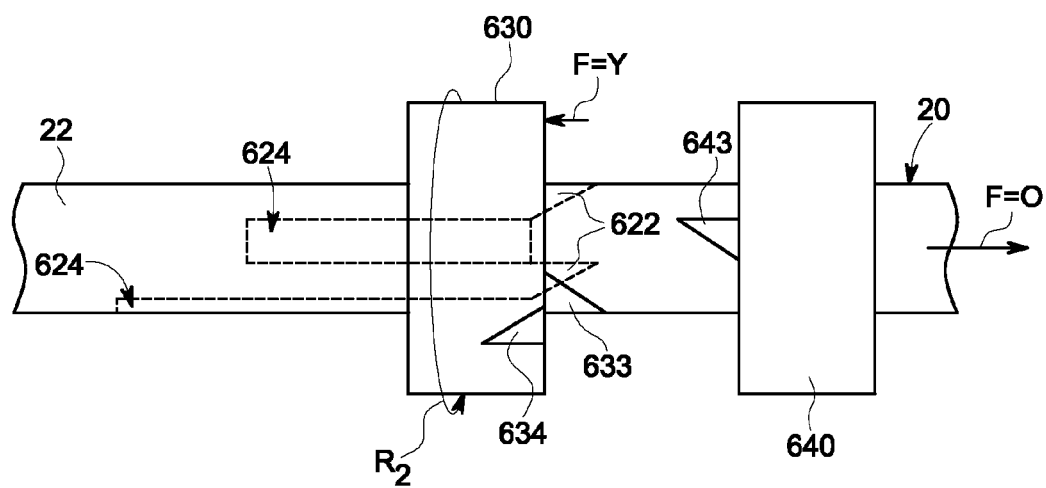
Figure 5D:
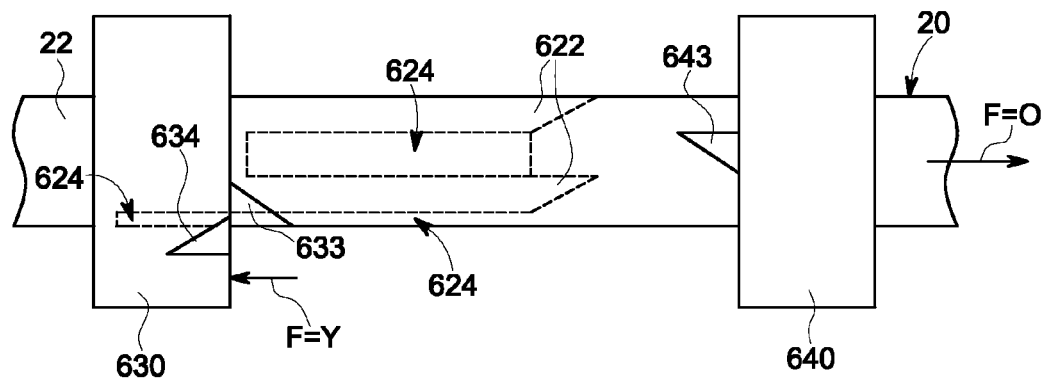

The abutment parts 643 and the first parts 633 have complementarily angled surfaces that induce rotation of the position collar 630 as the position collar 630 continues to be axially displaced. Once the pulling load is released and the force, F, being applied to the cable 20 by the cable unit 516 decreases to zero, as shown in FIGS. 5C and 5D, the position collar 630 is permitted to reversely axially displace in accordance with the force, Y, of the bias applied thereto by the elastic element 611. This reverse axial displacement results in the second parts 634 of the position collar 630 becoming once again rotationally constrained in the depth setting channels 624 only this time in the next one of the multiple orientations.

Depths of the depth setting channels 624 may vary from one another and govern an amount of reverse axial displacement of the position collar 630 that is permitted. That is, in a case where the position collar 630 has a single second part 634, the position collar 630 is permitted to reversely axially displace by different amounts or distances depending on which depth setting channel 624 the single second part 634 is aligned with and/or rotationally constrained in as the reverse axial displacement will continue until the second part 634 reaches the end of the depth setting channel 624. Thus, in one of the multiple orientations, the second part 634 may be aligned with and/or rotationally constrained in a relatively shallow depth setting channel 624 and, in another one of the multiple orientations, the second parts 634 may be aligned with and/or rotationally constrained in a relatively deep depth setting channel 624, as shown in FIG. 5D. Accordingly, the position collar 630 will be permitted to reversely axially displace further with the former one of the multiple orientations being assumed as compared to the latter being assumed. Concurrently, since the cable 20 is effectively positionally coupled to the position collar 630, the cable 20 will be seen as occupying one of the multiple rest positions based on which of the multiple orientations is assumed.

In accordance with various embodiments, the outer collar 620 and the position collar 630 may assume one of two or more orientations. For example, if the position collar 630 has a single second part 634 and the outer collar 620 defines eight depth setting channels 624 with eight different depths, eight orientations will be defined along with eight rest positions provided for the cable 20. By contrast, if the position collar 630 has two second parts 634, eight orientations will be defined along with four rest positions provided for the cable 20.

In accordance with further embodiments, the induced rotation of the position collar 630 can be caused by only the cooperation of the complementarily angled surfaces of the abutment parts 643 and the first parts 633 or, additionally, by cooperation of complementarily angled surfaces of the second parts 634 and the third parts 622 as illustrated by rotation, $R_2$, of FIG. 5C. In the latter case, half of the induced rotation may be provided by the cooperation of the complementarily angled surfaces of the abutment parts 643 and the first parts 633 and half of the induced rotation may be provided by cooperation of the complementarily angled surfaces of the second parts 634 and the third parts 622.

In the latter case discussed above, an operator seeking to image the object 40 in the first zoom state, Z1, and then the second zoom state, Z2, will first position the cable 20 and the device 30 such that the device 30 is proximate to the object 40, then generate an image of the object 40 with the cable 20 in the first rest position, R1, and then actuate the input unit 514 only once. This single actuation will cause the cable unit 516 to temporarily activate and, for example, pull the cable 20 with force, F, as described above and as shown in FIG. 5B, from the first rest position, R1, into the energized position, E, whereby the position collar 630 will have completed half the rotation toward the next orientation. The cable unit 516 will then deactivate to thereby allow the position collar 630 to reversely displace in accordance with the bias applied by the elastic element 611 such that the cable 20 will assume the second rest position, R2, whereby the position collar 630 will have completed the second half of the rotation toward the next (now current) orientation.

In accordance with further embodiments, it is to be understood that the abutment parts 643 and the first parts 633 could each be provided as singular or multiple parts. In the former case, the cable unit 516 would pull the cable 20 for a length of time sufficient to induce the required amount of rotation of the position collar 630.

In accordance with still further embodiments, it is to be understood that the input unit 514 could be provided as singular or multiple buttons. Where the input unit 514 is a singular button, a single actuation of the input unit 514 may be associated with a single activation/deactivation cycle of the cable unit 516. By contrast, multiple buttons of the input unit 514 could each be associated with single and multiple activation/deactivation cycles of the cable unit 516. Thus, if the operator wished to move the cable 20 from one rest position to another while skipping an intermediate rest position, the operator could still make a single actuation of one of the multiple buttons to do so. In such a case, the cable unit 516 would automatically activate and possibly deactivate in multiple stages to induce all of the required rotation of the position collar 630.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A cable apparatus, comprising:
   a cable comprising a first cable segment and a second cable segment;
   an actuator operably coupled to the cable and including a power source and a cable unit, the actuator, when activated, causes the second cable segment to translate in a first axial direction and draws power from the power source and, when deactivated, draws no power and permits the second cable segment to translate in a second opposite axial direction; and a housing operably disposed between the first cable segment and the second cable segment, the housing including a first element that rotates and translates with respect to the second cable segment and a second element fixed to the second cable segment, the first element being configured to cause the second element to rotate in relation to the first element, wherein the housing further comprises at least two channels, each channel having an associated depth, and wherein, when the second element is rotationally aligned with a channel of the at least two channels, the associated depth of the aligned channel limits the axial translation of the second element in the second opposite axial direction.

2. The cable apparatus according to claim 1, wherein each of the at least two channels is associated with a unique cable length.

3. The cable apparatus according to claim 1, wherein the actuator comprises a handheld device.

4. The cable apparatus according to claim 3, wherein the power source comprises a battery housed in the handheld device.

5. The cable apparatus according to claim 3, wherein the handheld device comprises an input unit by which a single command for activating the cable unit is receivable.

6. The cable apparatus according to claim 1, wherein activation of the cable unit comprises one or more activation and deactivation cycles.

7. The cable apparatus according to claim 1, wherein the cable unit affects the cable by one of mechanical action, electro-magnetism and thermal input.

8. A cable apparatus, comprising:

a cable comprising a first cable segment and a second cable segment;

a device disposed on the cable and configured to generate an image in first or second zoom states respectively associated with each position;

an actuator operably coupled to the cable and the device and including a power source, a display unit to display the image, and a cable unit, the actuator, when activated, causes the second cable segment to translate in a first axial direction and, when deactivated, draws no power and permits the second cable segment to translate in a second opposite axial direction; and a housing operably disposed between the first cable segment and the second cable segment, the housing including a first element that rotates and translates with respect to the second cable segment and a second element fixed to the second cable segment, the first element being configured to cause the second element to rotate in relation to the first element, where the housing further comprises at least two channels, each channel having an associated depth, and wherein, when the second element is rotationally aligned with a channel of the at least two channels, the associated depth of the aligned channel limits the axial translation of the second element in the second opposite axial direction.

9. The cable apparatus according to claim 8, wherein each of the at least two channels is associated with a unique cable length.

10. The cable apparatus according to claim 8, wherein the device comprises a camera.

11. The cable apparatus according to claim 8, wherein the actuator comprises a handheld device.

12. The cable apparatus according to claim 11, wherein the power source comprises a battery housed in the handheld device.

13. The cable apparatus according to claim 11, wherein the handheld device comprises an input unit by which a single command for activating the cable unit is receivable.

14. The cable apparatus according to claim 8, wherein activation of the cable unit comprises one or more activation/deactivation cycles.

15. The cable apparatus according to claim 8, wherein the cable unit affects the cable by one of mechanical action, electro-magnetism and thermal input.

16. A cable apparatus, comprising:

a cable comprising a first cable segment and a second cable segment;

an actuator operably coupled to the cable and including a power source and a cable unit, the actuator, when activated, causes the second cable segment to initially translate in a first axial direction from a first position to a second position and draws power from the power source and, when deactivated, draws no power and permits the second cable segment to secondarily translate in a second opposite axial direction from the second position to a third position; and a housing disposed between the first cable segment and the second cable segment, the housing including:

a first assembly to urge the second cable segment to secondarily translate from the second position to the third position, and a second assembly including a first element that rotates and translates with respect to the second cable segment and a second element fixed to the second cable segment, the first element being configured to cause the second element to rotate in relation to the first element to thereby urge the cable toward assumption of the third position, wherein the housing further comprises at least two channels, each channel having an associated depth, and wherein, when the second element is rotationally aligned with a channel of the at least two channels, the associated depth of the aligned channel limits the axial translation of the second element in the second opposite axial direction.

17. The cable apparatus according to claim 16, further comprising a device disposed on the cable to generate an image in first or second zoom states respectively associated with each of the first and third positions, wherein the actuator comprises a display unit to display the image.

18. The cable apparatus according to claim 16, wherein the actuator comprises:

a handheld device;

a battery housed in the handheld device; and an input unit by which a single command for activating the cable unit is receivable by the actuator.

19. The cable apparatus according to claim 17, wherein the first assembly comprises an elastic element to bias the second cable segment to secondarily translate and the second assembly comprises:

an outer collar formed to define the first and third positions;

a position collar, coupled to the cable, which is receivable by the outer collar in multiple orientations respectively associated with the first and third positions; and an indexing system to urge the position collar and the outer collar to rotate relative to one another.

20. The cable apparatus according to claim 1, where the first element comprises a first angled surface, the second element comprises a second angled surface, the first angled surface is complementarily to the second angled surface, and the first angled surface and the second angled surface cause the second element to rotate during the permitted cable translation.

* * * * *